(12) United States Patent
Park et al.

(10) Patent No.: US 11,092,441 B2
(45) Date of Patent: Aug. 17, 2021

(54) SYSTEMS AND METHODS FOR WALKING SPEED ESTIMATION

(71) Applicant: Bigmotion Technologies Inc., Surrey (CA)

(72) Inventors: Jung Wook Park, Surrey (CA); Shaghayegh Zihajehzadeh, Burnaby (CA)

(73) Assignee: BigMotion Technologies Inc., Surrey (CA)

( * ) Notice: Subject to any disclaimer, the term of this patent is extended or adjusted under 35 U.S.C. 154(b) by 436 days.

(21) Appl. No.: 16/306,405

(22) PCT Filed: Jun. 1, 2017

(86) PCT No.: PCT/CA2017/050669
§ 371 (c)(1),
(2) Date: Nov. 30, 2018

(87) PCT Pub. No.: WO2017/205983
PCT Pub. Date: Dec. 7, 2017

(65) Prior Publication Data
US 2020/0149894 A1 May 14, 2020

Related U.S. Application Data

(60) Provisional application No. 62/344,566, filed on Jun. 2, 2016.

(51) Int. Cl.
*G01C 21/18* (2006.01)
*G01P 3/50* (2006.01)
*G06K 9/00* (2006.01)

(52) U.S. Cl.
CPC ............... *G01C 21/18* (2013.01); *G01P 3/50* (2013.01); *G06K 9/00348* (2013.01); *G06K 9/00523* (2013.01)

(58) Field of Classification Search
CPC .. G01C 21/18; G01P 3/50; G01P 7/00; G06K 9/00348; G06K 9/00523
See application file for complete search history.

(56) References Cited

U.S. PATENT DOCUMENTS 4,578,769 A * 3/1986 Frederick .................. G01P 3/50
  702/160
5,955,667 A * 9/1999 Fyfe ..................... A61B 5/1038
  73/490

(Continued)

FOREIGN PATENT DOCUMENTS

CA     2329368 A1    6/1997
EP     1366712 A1   12/2003

OTHER PUBLICATIONS

Zhou et al., "Kinematic model aided inertial motion tracking of human upper limb" in Information Acquisition, 2005 IEEE nternational Conference on, IEEE, 2005, pp. 150-155.

(Continued)

*Primary Examiner* — Babar Sarwar
(74) *Attorney, Agent, or Firm* — Norton Rose Fulbright Canada LLP; Maya Medeiros

(57) ABSTRACT

Systems and methods are provided for estimating a walking speed of a subject. A method comprises mounting an inertial measurement unit (IMU) on a wrist of the subject, the IMU configured to generate acceleration and rate of turn signals; processing the acceleration and rate of turn signals from the IMU to generate a pitch angle and a roll angle; processing the pitch angle and the roll angle to generate a rotation matrix from a sensor frame of the IMU to a navigation frame of the subject; applying the rotation matrix to the acceleration signals and removing gravitational acceleration to generate an external acceleration signal; processing the external acceleration signal to determine a principal horizontal axis and to generate a principal component acceleration signal (Continued)

representing external acceleration along the principal horizontal axis; and processing the principal component acceleration signal using a regression-based method to determine an estimated walking speed of the subject.

10 Claims, 6 Drawing Sheets

(56) References Cited

U.S. PATENT DOCUMENTS

| | | | | |
|---|---|---|---|---|
| 6,356,856 | B1* | 3/2002 | Damen | A43B 3/00 482/3 |
| 6,876,947 | B1* | 4/2005 | Darley | A61B 5/1118 702/160 |
| 7,237,446 | B2* | 7/2007 | Chan | A63B 69/0028 73/509 |
| 7,373,820 | B1* | 5/2008 | James | A61B 5/0002 340/573.1 |
| 7,648,441 | B2* | 1/2010 | Silk | A61B 5/7415 482/1 |
| 8,744,783 | B2* | 6/2014 | Templeman | G01L 1/26 702/44 |
| 9,198,604 | B2 | 12/2015 | Venkatraman et al. | |
| 2004/0094613 | A1* | 5/2004 | Shiratori | A61B 5/681 235/105 |
| 2008/0262772 | A1* | 10/2008 | Luinge | A61B 5/1114 702/94 |
| 2008/0284784 | A1* | 11/2008 | Liu | G06T 13/40 345/474 |
| 2008/0285805 | A1* | 11/2008 | Luinge | A61B 5/1122 382/107 |
| 2010/0214216 | A1* | 8/2010 | Nasiri | A63F 13/211 345/158 |
| 2012/0136573 | A1* | 5/2012 | Janardhanan | G01C 21/20 701/512 |
| 2012/0155775 | A1* | 6/2012 | Ahn | G05D 1/0272 382/195 |
| 2013/0046505 | A1* | 2/2013 | Brunner | G01C 22/006 702/141 |
| 2013/0090881 | A1* | 4/2013 | Janardhanan | G06F 1/163 702/104 |
| 2013/0217998 | A1* | 8/2013 | Mahfouz | A61B 8/4263 600/409 |
| 2013/0262024 | A1* | 10/2013 | Sakurai | G10H 1/0008 702/150 |
| 2015/0032408 | A1* | 1/2015 | Grenet | A61B 5/1116 702/141 |
| 2015/0354967 | A1* | 12/2015 | Matsushita | G01C 21/165 702/150 |
| 2015/0375108 | A1* | 12/2015 | Pathirana | A63F 13/235 463/39 |
| 2016/0029943 | A1* | 2/2016 | Mizuochi | A61B 5/0022 702/141 |
| 2016/0116995 | A1* | 4/2016 | Wilson | G06F 3/011 345/157 |
| 2016/0161254 | A1* | 6/2016 | Nakajima | A61B 5/1116 702/151 |
| 2016/0216130 | A1* | 7/2016 | Abramson | G01C 21/3423 |
| 2017/0076619 | A1* | 3/2017 | Wallach | G09B 19/0038 |
| 2017/0281056 | A1* | 10/2017 | Raanan | A61B 5/6831 |
| 2018/0180443 | A1* | 6/2018 | Han | H04W 4/029 |
| 2019/0056422 | A1* | 2/2019 | Park | A63F 13/212 |

OTHER PUBLICATIONS

Park, J., "Synthesis of natural arm swing motion in human bipedal walking", Journal of Biomechanics 41 (2008), pp. 1417-1426.

Vathsangam et al., "Toward Free-Living Walking Speed Estimation Using Gaussian Process-based Regression with On-Body Accelerometers and Gyroscopes", Pervasive Computing Technologies for Healthcare (PervasiveHealth), 2010 4th International Conference on, Mar. 22-25, 2010, DOI: 10.4108/ICST.PERVASIVEHEALTH2010. 8786.

Renaudin et al., "Step Length Estimation Using Handheld Inertial Sensors", Sensors 2012, 12, doi: 10.3390/s120708507, pp. 8507-8525.

Park et al., "Online pose classification and walking speed estimation using handheld devices", Proceeding UbiComp 12 Proceedings of the 2012 ACM Conference on Ubiquitous Computing, DOI 10.1145/2370216.2370235, Sep. 5-8, 2012, pp. 113-122.

Dadashi et al., "Inertial measurement unit and biomechanical analysis of swimming: an update", Swiss Society of Sports Medecine, vol. 61, 2013, pp. 21-26.

Zhang et al., "A Handheld Inertial Pedestrian Navigation System With Accurate Step Modes and Device Poses Recognition", IEEE Sensors Journal, vol. 15, No. 3, Mar. 2015, pp. 1421-1429.

Ligorio et al., "A Novel Kalman Filter for Human Motion Tracking With an Inertial-Based Dynamic Inclinometer", IEEE Transactions on Biomedical Engineering, vol. 62, No. 8, Aug. 2015, pp. 2033-2043.

Bertschi et al., "Accurate walking and running speed estimation using wrist inertial data", Engineering in Medicine and Biology Society (EMBC), 2015 37th Annual International Conference of the IEEE, Aug. 25-29, 2015, DOI: 10.1109/EMBC.2015.7320269, pp. 8083-8086.

Zihajehzadeh et al., "Regression Model-Based Walking Speed Estimation Using Wrist-Worn Inertial Sensor", PLOS One, Oct. 20, 2016, DOI:10.1371/journal.pone.0165211, pp. 1/16-16/16.

Duong et al., "Walking Parameters Estimation Based on a Wrist-Mounted Inertial Sensor for a Walker User", IEEE Sensors Journal, vol. 17, No. 7, Apr. 1, 2017, pp. 2100-2108.

International Search Report and Written Opinion dated Sep. 18, 2017, issued in connection with international application No. PCT/CA2017/050669.

International Preliminary Report on Patentability dated Sep. 4, 2018, issued in connection with international application No. PCT/CA2017/050669.

Akl et al.; Autonomous Unobtrusive Detection of Mild Cognitive Impairment in Older Adults; IEEE Transactions on Biomedical Engineering, vol. 62, No. 5, May 2015.

Dodge et al.; In-home walking speeds and variability trajectories associated with mild cognitive impairment; Neurology 2012, 78:1946-1952.

Ahmad Akl and Alex Mihailidis; Estimating In-home Walking Speed Distributions for Unobtrusive Detection of Mild Cognitive Impairment in Older Adults; Annu Int Conf IEEE Eng Med Biol Soc. 2015, 2015:5175-8.

Heesen et al.; Patient perception of bodily functions in multiple sclerosis: gait and visual function are the most valuable; Multiple Sclerosis 2008, 14(7):988-91.

Graham et al.; Assessing walking speed in clinical research: a systematic review; Journal of Evaluation in Clinical Practice, Aug. 2008, vol. 14, No. 4, pp. 552-562.

Bayle et al.; Contribution of Step Length to Increase Walking and Turning Speed as a Marker of Parkinson's Disease Progression; Apr. 2016, PLoS One 11(4): e0152469.

Bautmans et al.; Reliability and clinical correlates of 3D-accelerometry based gait analysis outcomes according to age and fall-risk; Gait & Posture 33 (2011) 366-372.

Abe et al.; Determinants of Slow Walking Speed in Ambulatory Patients Undergoing Maintenance Hemodialysis; Mar. 2016, PLoS One 11(3): e0151037.

Robertson et al.; Negative Perceptions of Aging and Decline in Walking Speed: A Self-Fulfilling Prophecy; Apr. 2015, PLoS One 10(4): e0123260.

Stacy Fritz and Michelle Lusardi; White Paper: "Walking Speed: the Sixth Vital Sign"; 2009, Journal of Geriatric Physical Therapy, vol. 32, Issue 2, pp. 2-5.

Studenski et al.; Gait Speed and Survival in Older Adults; JAMA, Jan. 5, 2011—vol. 305, No. 1, pp. 50-58.

Maggio et al.; Instrumental and Non-Instrumental Evaluation of 4-Meter Walking Speed in Older Individuals; Apr. 2016, PLoS One 11(4): e0153583.

(56) References Cited

OTHER PUBLICATIONS

Schimpl et al.; Development and Validation of a New Method to Measure Walking Speed in Free-Living Environments Using the Actibelt® Platform; Aug. 2011, PLoS One 6(8): e23080.
Barry R. Greene and Rose A. Kenny; Assessment of Cognitive Decline Through Quantitative Analysis of the Timed Up and Go Test; IEEE Transactions on Biomedical Engineering, vol. 59, No. 4, Apr. 2012.
Vaney et al.; Assessing mobility in multiple sclerosis using the Rivermead Mobility Index and gait speed; Clinical Rehabilitation 1996, 10(3):216-226.
Enright et al.; The 6-min Walk Test: A Quick Measure of Functional Status in Elderly Adults; Chest, Feb. 2003, vol. 123, Issue 2, pp. 387-98.
Schimpl et al.; Association between Walking Speed and Age in Healthy, Free-Living Individuals Using Mobile Accelerometry—A Cross-Sectional Study; Aug. 2011, PLoS One 6(8): e23299.
Hagler et al.; Unobtrusive and Ubiquitous In-Home Monitoring: A Methodology for Continuous Assessment of Gait Velocity in Elders; IEEE Transactions on Biomedical Engineering, vol. 57, No. 4, Apr. 2010.
Jacobs et al.; Measuring In-Home Walking Speed using Wall-Mounted RF Transceiver Arrays; Conf Proc IEEE Eng Med Biol Soc. Aug. 2014; 2014:914-917.
Wang et al.; Toward a Passive Low-Cost In-Home Gait Assessment System for Older Adults; IEEE Journal of Biomedical and Health Informatics, vol. 17, No. 2, Mar. 2013.
Shaghayegh Zihajehzadeh and Edward J. Park; A Novel Biomechanical Model-Aided IMU/UWB Fusion for Magnetometer-Free Lower Body Motion Capture; IEEE Transactions on Systems, Man, and Cybernetics: Systems, vol. 47, No. 6, Jun. 2017.
Loh et al.; Fitness Activity Classification by Using Multiclass Support Vector Machines on Head-worn Sensors; Annu Int Conf IEEE Eng Med Biol Soc. Aug. 2015; 2015:502-5.
Jung Keun Lee and Edward J. Park; A Fast Quatemion-Based Orientation Optimizer via Virtual Rotation for Human Motion Tracking; IEEE Transactions on Biomedical Engineering, vol. 56, No. 5, May 2009.
Elhoushi et al.; Motion Mode Recognition for Indoor Pedestrian Navigation Using Portable Devices; IEEE Transactions on Instrumentation and Measurement, vol. 65, No. 1, Jan. 2016.
Laudanski et al;. A Concurrent Comparison of Inertia Sensor-Based Walking Speed Estimation Methods; Annu Int Conf IEEE Eng Med Biol Soc. 2011, 2011:3484-7.
Zihajehzadeh et al.; A cascaded Kalman filter-based GPS/MEMS-IMU integration for sports applications; Measurement 7-3 (2015) 200-210.
Eric Foxlin; Pedestrian Tracking with Shoe-Mounted Inertial Sensors; IEEE Computer Graphics and Applications, vol. 25, No. 6, pp. 38-46, Nov.-Dec. 2005.
Meng et al.; Hierarchical Information Fusion for Global Displacement Estimation in Microsensor Motion Capture; IEEE Transactions on Biomedical Engineering, vol. 60, No. 7, Jul. 2013.
Skog et al.; Zero-Velocity Detection—An Algorithm Evaluation; IEEE Transactions on Biomedical Engineering, vol. 57, Issue 11, pp. 2657-2666, Nov. 2010.
Hu et al.; A Kinematic Human-Walking Model for the Normal-Gait-Speed Estimation Using Tri-Axial Acceleration Signals at Waist Location; IEEE Transactions on Biomedical Engineering, vol. 60, No. 8, Aug. 2013.
Dadashi et al.; A Bayesian approach for pervasive estimation of breaststroke velocity using a wearable IMU; Pervasive and Mobile Computing 19 (2015) 37-46.
Carl Edward Rasmussen and Christopher K.I. Williams; Gaussian Processes for Machine Learning; MIT Press, 2006.
Vathsangam et al.; An Experimental Study in Determining Energy Expenditure from Treadmill Walking using Hip-Worn Inertial Sensors; IEEE Trans Biomed Eng. Oct. 2011; 58(10): 2804-2815.
Robert Tibshirani; Regression Shrinkage and Selection via the Lasso; Journal of the Royal Statistical Society, Series B (Methodological), vol. 58, No. 1, pp. 267-288, 1996.
Zihajehzadeh et al.; A Cascaded Two-Step Kalman Filter for Estimation of Human Body Segment Orientation Using MEMS-IMU; 2014 36th Annual International Conference of the IEEE Engineering in Medicine and Biology Society, Chicago, IL, USA, 2014, pp. 6270-6273.
Zihajehzadeh et al.; Integration of MEMS Inertial and Pressure Sensors for Vertical Trajectory Determination; IEEE Transactions on Instrumentation and Measurement, vol. 64, No. 3, Mar. 2015.
Lee et al.; Estimation of Attitude and External Acceleration Using Inertial Sensor Measurement During Various Dynamic Conditions; IEEE Transactions on Instrumentation and Measurement, vol. 61, No. 8, Aug. 2012.
Ian T. Jolliffe; Principal Component Analysis; 2002, Springer-Verlag New York.
Vathsangam et al.; Towards a Generalized Regression Model for On-body Energy Prediction from Treadmill Walking; 2011 5th International Conference on Pervasive Computing Technologies for Healthcare (PervasiveHealth) and Workshops, Dublin, Ireland, 2011, pp. 168-175.

\* cited by examiner

SYSTEMS AND METHODS FOR WALKING SPEED ESTIMATION

CROSS REFERENCE TO RELATED APPLICATION

This application claims the benefit of priority of U.S. Provisional Patent Application No. 62/344,566 filed on Jun. 2, 2016, which is hereby incorporated herein by reference in its entirety.

TECHNICAL FIELD

The present disclosure relates to wearable sensors for determining the motion of a subject, and in particular estimation of a subject's walking speed.

BACKGROUND

Walking speed is a fundamental indicator of human health status. Based on previous studies, walking speed can be used as a vital sign to predict mild cognitive impairment (MCI), multiple sclerosis (MS), Parkinson's disease, chronic obstructive pulmonary disease (COPD) and risk of falls. Hence, walking speed can be considered as a powerful predictor of hospitalization, disability and survival. In a clinical setting, different protocols including the 10-meter, 500-meter, and 6-minute walking tests, and the timed up and go (TUG) test, have been used as standard tools to evaluate walking speed and gait parameters. However, the short walking tests (e.g., the 10-meter walking test) are subject to bias due to their brevity, and the longer tests are less accepted due to the space and time constraints in clinical exams. Additionally, walking speed results of the clinical tests cannot be fully applied to free-living environments. This emphasizes the need for a reliable system/method for longitudinal (and continuous) walking speed measurement in real-world situations.

Aiming at longitudinal walking speed measurement outside the clinical setting, some researchers have used passive infrared (PIR) motion sensors. These PIR sensors can be mounted on ceiling or walls of a residence and can measure the individuals' walking speed when they are in the field of view of the sensors. However, walking speed measurement based on PIR sensors is limited to confined areas such as hallways. Additionally, such a system cannot differentiate between multiple residents, limiting its application to independent-living resident homes. Camera-based systems have also been used in the literature for in-home gait speed measurement. However, camera-based systems can get affected by the lighting conditions, and similar to the PIR sensors, they are limited to confined areas and hence more suitable for the clinical settings.

With recent advances in the MEMS sensor technology, wearable inertial measurement units (IMUs) have emerged as powerful devices for portable human motion analysis. Being self-contained, wearable inertial sensors can facilitate walking speed measurement in an ambulatory fashion. Considering that the acceleration data from a tri-axial accelerometer in a wearable inertial sensor can be integrated to get the velocity, integration-based approaches have been widely used for speed tracking. A significant challenge in the integration-based approaches is the velocity drift over time that happens as a result of time-varying bias in MEMS-based inertial sensors.

To mitigate the drift, some researchers have proposed the detection of periodic foot stance phases during walking to reset the velocity to zero through a process called zero velocity update (ZUPT). However, the need for foot-stance detection requires the wearable sensor to be normally mounted on the leg (ideally on the foot), which is inconvenient for longitudinal walking speed monitoring, particularly indoors. Using waist-worn IMU, some studies have modeled the foot swing in walking as an inverted pendulum in order to find a 3D walking kinematic model for speed estimation. Additionally, using a waist-mounted IMU, linear and non-linear regression models have shown promising performances for ambulatory walking and swimming speed estimation. These regression-based approaches for walking speed estimation are based on mapping the inherent pattern of acceleration and rate of turn information corresponding to the hip rotation in a gait cycle to walking speed.

SUMMARY

One aspect provides a system for estimating walking speed of a subject. The system comprises an inertial measurement unit (IMU) mounted on a wrist of the subject, and a processing system in communication with the IMU. The IMU comprises an accelerometer and a gyroscope and configured to output rate of turn signals and acceleration signals. The processing system comprises: a sensor fusion block configured to process the rate of turn and acceleration signals from the IMU to generate a pitch angle and a roll angle; a rotation matrix calculation block configured to process the pitch angle and the roll angle to generate a rotation matrix from a sensor frame of the IMU to a navigation frame of the subject; an acceleration vector transformation block configured to apply the rotation matrix to the acceleration signals and remove gravitational acceleration to generate an external acceleration signal; a principal component analysis block configured to process the external acceleration signal to determine a principal horizontal axis; a principal component extraction block configured to process the external acceleration signal to generate a principal component acceleration signal representing external acceleration along the principal horizontal axis; and a walking speed estimation block configured to process the principal component acceleration signal using a regression-based method to determine an estimated walking speed of the subject.

Another aspect provides a method for estimating a walking speed of a subject. The method comprises: mounting an inertial measurement unit (IMU) on a wrist of the subject, the IMU configured to generate acceleration signals and rate of turn signals; processing the acceleration and rate of turn signals from the IMU to generate a pitch angle and a roll angle; processing the pitch angle and the roll angle to generate a rotation matrix from a sensor frame of the IMU to a navigation frame of the subject; applying the rotation matrix to the acceleration signals and removing gravitational acceleration to generate an external acceleration signal; processing the external acceleration signal to determine a principal horizontal axis and to generate a principal component acceleration signal representing external acceleration along the principal horizontal axis; and processing the principal component acceleration signal using a regression-based method to determine an estimated walking speed of the subject.

Further aspects and details of example embodiments are set forth below.

DRAWINGS

The following figures set forth embodiments in which like reference numerals denote like parts. Embodiments are illustrated by way of example and not by way of limitation in the accompanying figures.

FIG. 1A is a photograph showing an experimental setup for testing a prototype walking speed estimation system according to one embodiment.

FIG. 1B schematically illustrates a test field used with the experimental setup of FIG. 1A.

DETAILED DESCRIPTION

Figure 1A:
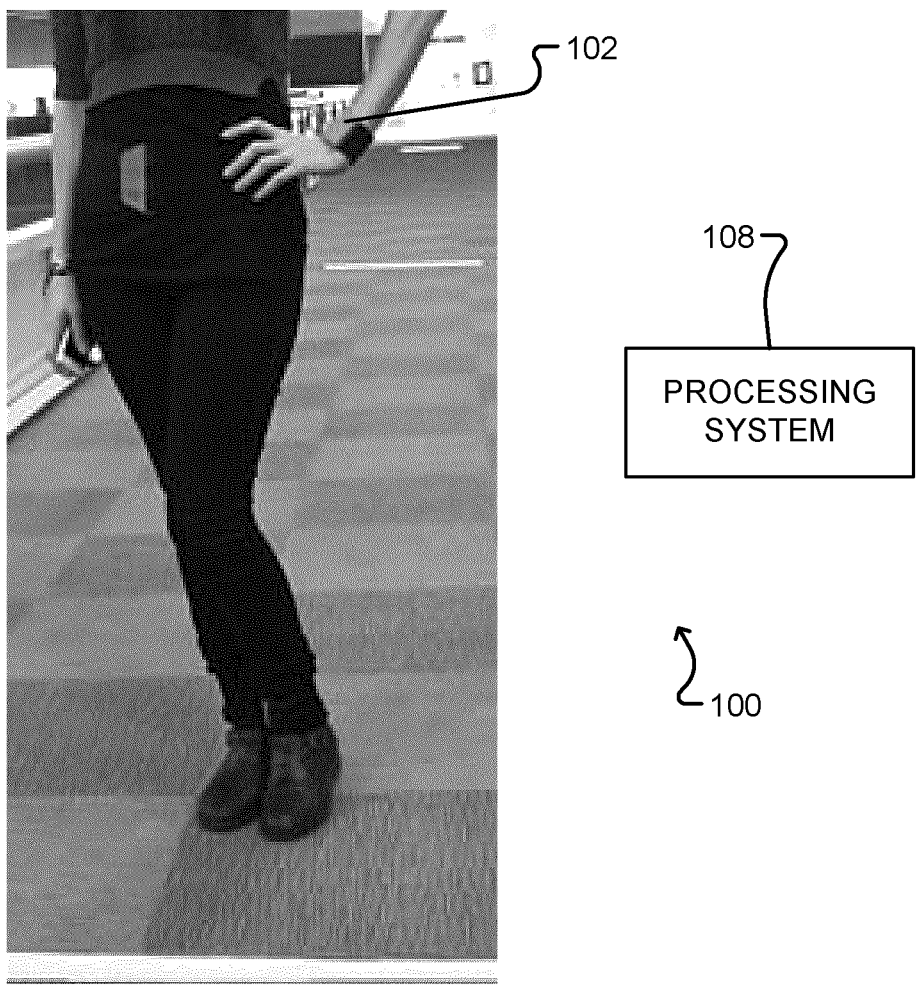

The present disclosure provides systems and methods for estimating a subject's walking speed using an inertial measurement unit (IMU) mounted on the subject's wrist. Wearable IMUs are promising tools for ambulatory measurement of walking speed. For longitudinal health status monitoring, among available state-of-the-art inertial wearable choices, wrist-worn devices are the most user-friendly and compliant that do not limit the freedom of movement and do not require specific dressing style (e.g., wearing a belt for the case of waist-worn sensor). Thus, wrist-worn devices have relatively higher potential to be easily incorporated into daily lifestyle and worn for longer hours. Although walking speed estimation based on waist or foot-worn sensors is relatively straight forward, accurate walking speed estimation using only a wrist-worn IMU is not as straightforward.

Similar to hip rotation in each gait cycle, arm swing motion during walking is a periodic motion pattern that is highly correlated to walking speed: the faster the walking speed, the faster the arm swing motion. However, in walking speed estimation based on regression models, accuracy can be improved by the use of more complex signal processing to manipulate the acceleration and rate of turn signals to determine a variable that is more representative of the arm swing motion. Although extracting this variable is of high importance (since the accuracy of the regression models depends on the set of chosen variables and the extracted features), it has not been addressed in the existing literature.

Aiming at accurate walking speed estimation using a wrist-worn IMU, the present disclosure provides novel signal processing systems and methods based on combined inertial sensor fusion and principal component analysis (PCA) for the variable extraction. By using the arm swing motion in walking, the present disclosure proposes regression model-based systems and methods for longitudinal walking speed estimation using a wrist-worn IMU. To make the best use of arm swing's inertial information, a novel kinematic variable, referred to herein as "pca-acc," is proposed that describes the wrist acceleration in the principal axis (i.e. the direction of the arm swing). A principal component acceleration signal representing this pca-acc variable is obtained by applying sensor fusion methods to tri-axial accelerometer and gyroscope data to find the tilt angles followed by further processing including the use of principal component analysis, as discussed below. The obtained signal is then used to estimate walking speed by applying a regression model that determines walking speed from the principal component acceleration signal.

For simplicity and clarity of illustration, reference numerals may be repeated among the figures to indicate corresponding or analogous elements. Numerous details are set forth to provide an understanding of the examples described herein. The examples may be practiced without these details. In other instances, well-known methods, procedures, and components are not described in detail to avoid obscuring the examples described. The description is not to be considered as limited to the scope of the examples described herein.

Experimental Setup

An experimental evaluation of a prototype walking speed estimation system was performed on 15 healthy subjects during free walking trials. Experimental results, discussed in more detail below, show that the extracted principal component acceleration signal can improve the accuracy of wrist-based walking speed estimation. In particular, the results show that the use of the proposed systems and methods can significantly improve the walking speed estimation accuracy when compared against the use of raw acceleration information. When Gaussian process regression (GPR) is used, the resulting walking speed estimation accuracy and precession is about 5.9% and 4.7% respectively.

FIG. 1A shows an example experimental system 100 for estimating walking speed of a subject. The system 100 comprises a wrist-mounted IMU 102 and a processing system 108 in communication with the IMU 102. The IMU 102 comprises a tri-axial gyroscope and a tri-axial accelerometer, and generates rate of turn signals and acceleration signals which are provided to the processing system 108, preferably by means of a wireless communication protocol. In the experimental system 100 the IMU 102 comprises a MTw™ wireless motion sensor manufactured by Xsens™, and raw inertial data is collected from the tri-axial accelerometers and tri-axial gyroscopes of the IMU 102 at the rate of 100 Hz.

Figure 1B:
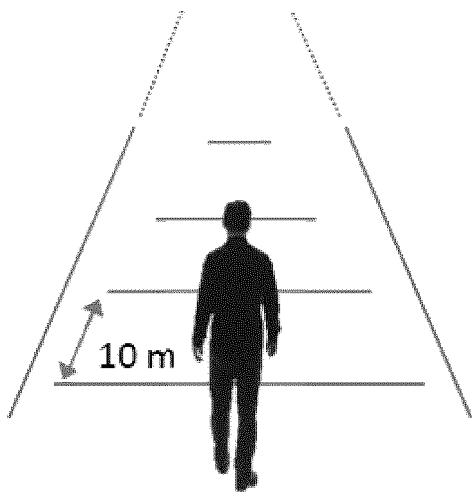

Each subject is asked to walk for a distance of 30 m in indoor environment for a total of 12 times in 3 different self-selected walking speed regimes: slow, normal and fast. The subjects are asked to keep their walking speed constant during each 30 m trial and each trial is repeated for 4 times per chosen speed regime. To get the ground truth average walking speed, the floor is divided into three segments of 10 m long (accurately measured by a laser distance measuring tool with sub-centimeter accuracy) as shown in FIG. 1B, and the time it takes for the subject to pass each segment is measured using a stopwatch with an accuracy of 0.01 s. Additionally, using the same sensor settings, one subject is asked to perform a 10-minute walking trial in an outdoor environment, including 4 min of fast walking and 6 min of normal walking. In this outdoor trial, an Xsens MTi-G-700 (consisting of tri-axial accelerometers, tri-axial gyroscopes, tri-axial magnetometers and the Global Positioning System (GPS)) is worn by the subject on her left wrist and a reference walking speed is obtained by GPS/IMU fusion methods using existing Kalman filter-based fusion techniques as described in Zihajehzadeh S, Loh D, Lee T J, Hoskinson R, Park E J. "A cascaded Kalman filter-based GPS/MEMS-IMU integration for sports applications." *Measurement*. 2015; 73: 200-210, which is hereby incorporated by reference herein. Compared to the indoor trials, this outdoor trial covers longer walking distance and duration and the subject has the freedom to change her walking direction. Thus, the outdoor experiment can be used to investigate the effect of direction changes on inertial variables. The processing system 108 is configured to implement methods and systems for walking speed estimation according to the present disclosure, as well as more simplistic walking speed estimation techniques, for comparison purposes, as discussed further below.

EXAMPLE SYSTEMS AND METHODS

Example System

Figure 2:
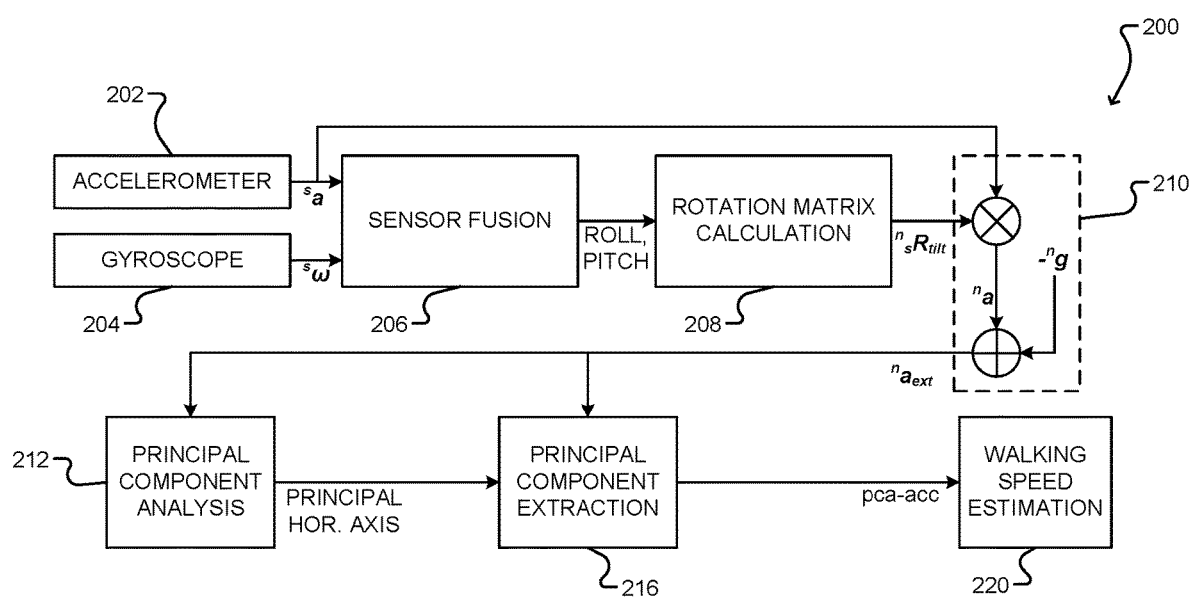
FIG. 2 is a block diagram schematically illustrating components of an example walking speed estimation system according to one embodiment.

FIG. 2 shows the overall structure of an example walking speed system 200 according to one embodiment of the present disclosure. The system 200 comprises an accelerometer input 202 for receiving acceleration signals from a wrist-mounted IMU to generate a tri-axial acceleration vector signal $^s a$ representing the measured accelerations in a sensor coordinate frame (the s-frame) attached to the IMU sensors, and a gyroscope input 204 for receiving rate of turn signals from the wrist-mounted IMU to generate a tri-axial rate of turn vector signal $^s \omega$ representing the measured rates of turn in the s-frame. In some embodiments, the sensor data from the IMU are low-pass filtered using a Butterworth filter with a cut-off frequency of 20 Hz considering that activities of daily living (ADL) fall in the frequency range of 0.1-10 Hz.

The raw data (or filtered raw data) from the sensors of the IMU may be used to generate signals representing three different variables: magnitude of 3D acceleration (acc), magnitude of external acceleration (ext-acc) and external acceleration in the principal axis (pca-acc). In the example system 200 shown in FIG. 2, the latter variable (pca-acc) is used for estimation of walking speed. The other two variables are arrived at with less advanced signal processing techniques and less representative of the arm swing during walking, and are used for comparison purposes in FIGS. 4-5 and Table 1 discussed below. The magnitude of the 3D acceleration (acc) is simply the norm (square root of the sum of squares) of the measured acceleration components:

$$\mathrm{acc} = |^s a| = \sqrt{^s a_x^2 + {^s a_y^2} + {^s a_z^2}} \quad (1)$$

where $^s a_i$, i=x, y, z is the acceleration measured by each axis of the accelerometer in the s-frame.

The magnitude of the 3D external acceleration (ext-acc) is the norm of gravity compensated acceleration (also known as external acceleration). Removing the gravity component from the tri-axial accelerometer data, which is done by the initial processing blocks of the system 200 of FIG. 2, results in a signal that represents the pure acceleration of the arm during walking. Considering the problem of walking speed estimation based on hand swing motion, one of the main shortcomings of using a parameter based on an external acceleration vector signal $^n a_{ext}$ (the generation of which is discussed below) for walking speed estimation is its dependency on the direction of hand swing motion in the navigation frame. The first issue is the inter-subject variability of the hand swing angle (i.e. for the same walking speed, the direction of hand swing with respect to the forward direction of motion varies between individuals). The second issue is the intra-subject variability for different walking directions (i.e. for the same walking speed, any changes in the walking direction results in a change in the absolute direction of the hand swing in the navigation frame). In the above mentioned two scenarios, variation in the direction of hand swing results in changes in the components of $^n a_{ext}$, which will in turn affect the ext-acc parameter. However, for a constant speed, the direction of hand swing should not affect the estimation of walking speed significantly. Thus, the present disclosure provides systems and methods that use pca-acc as a hand-swing-direction independent signal for estimating walking speed. This signal represents the horizontal external acceleration in the direction of its highest variations.

Returning to FIG. 2, the signals from the accelerometer and gyroscope inputs 202 and 204 are provided to a sensor fusion block 206 to determine roll and pitch angles, which are in turn provided to a rotation matrix calculation block 208 to generate a rotation matrix from the s-frame to a navigation coordinate frame (n-frame) with its x- and y-axes in a horizontal plane and its z-axis aligned with the gravity vector. The resulting rotation matrix $_s^n R_{tilt}$ is used by an acceleration vector transformation block 210 to represent the acceleration in the n-frame ($^n a$) and remove the gravity component to generate the external acceleration vector signal $^n a_{ext}$.

The sensor fusion block 206 determines roll and pitch angles (which may collectively be referred to as "tilt angles") of the wrist-mounted IMU using filtering techniques disclosed in S. Zihajehzadeh, D. Loh, M. Lee, R. Hoskinson, and E. J. Park, "A cascaded two-step Kalman filter for estimation of human body segment orientation using MEMS-IMU," *Proc. Annu. Int. Conf. IEEE Eng. Med. Biol. Soc.*, Chicago, USA, August 2014, pp. 6270-6273; S. Zihajehzadeh, T. J. Lee, J. K. Lee, R. Hoskinson, and E. J. Park, "Integration of MEMS Inertial and Pressure Sensors for Vertical Trajectory Determination," *IEEE Trans. Instrum. Meas.*, vol. 64, no. 3, pp. 804-814, March 2015; and J. K. Lee, E. J. Park, and S. Robinovitch, "Estimation of attitude and external acceleration using inertial sensor measurement during various dynamic conditions," *IEEE Trans. Instrum. Meas.*, vol. 61, no. 8, pp. 2262-2273, August 2012, which are hereby incorporated by reference herein.

The sensor fusion block 206 outputs the roll and pitch angles to the rotation matrix calculation block 208. The rotation matrix calculation block 208 calculates the rotation matrix $_s^n R_{tilt}$ using techniques disclosed in J. K. Lee, E. J. Park, and S. Robinovitch, "Estimation of attitude and external acceleration using inertial sensor measurement during various dynamic conditions," *IEEE Trans. Instrum. Meas.*, vol. 61, no. 8, pp. 2262-2273, August 2012.

The rotation matrix $_s^n R_{tilt}$ is applied to the acceleration vector signal $^s a$ to generate a vector signal representing the acceleration in the n-frame $^na$, and the gravity component of the acceleration is then removed in the acceleration vector transformation block 210:

$$^na_{ext} = {^nR_{tilt}}{^sa} - {^ng} \quad (2)$$

where $^na_{ext}$ and $^ng$ are the tri-axial external acceleration vector signal and the gravity vector signal respectively, both in the n-frame. The ext-acc variable referred to above may be calculated from the external acceleration vector signal $^na_{ext}$, as follows:

$$\text{ext-acc} = |^na_{ext}| = \sqrt{^na_{ext,x}^2 + {^2a_{ext,y}^2} + {^2_{ext,z}}} \quad (3)$$

In the system 200 of FIG. 2, the external acceleration vector signal $^na_{ext}$ is provided to a principal component analysis (PCA) block 212. The PCA block 212 applies techniques as described in I. T. Jolliffe, *Principal Component Analysis*. New York: Springer Verlag, 2002, which is hereby incorporated by reference herein, to the first two components (x- and y-components) of the external acceleration vector signal $^na_{ext}$ to determine the direction of highest acceleration variation in the horizontal plane. This direction is referred to herein as the principal horizontal axis.

The principal horizontal axis is provided to a principal component extraction block 216, which determines the first principal component of the external acceleration and generates a principal component acceleration signal representing the pca-acc variable, which is the external acceleration along the principal horizontal axis. The principal component extraction block 216 outputs the principal component acceleration signal (pca-acc) to a walking speed estimation block 220.

The walking speed estimation block 220 uses the principal component acceleration signal in the horizontal plane (pca-acc) for estimating walking speed using a suitable regression model. The following provides some theoretical discussion of estimating walking speed with regression-based methods and explains certain details of two example regression models: Gaussian process regression (GPR) and regularized least square regression using Lasso (LSR-Lasso).

Regression-Based Estimation of Walking Speed

Considering that walking is represented by a set of features, this section is focused on formulating a mapping from walking-related features (predictors) to walking speed (response value) using a regression model. In a regression problem, a training set ($\mathcal{S}$) consisting of N-number of D-dimensional predictors $x_i$ and noisy observations of the response value $y_i$ is given ($\mathcal{S} = \{(x_i, y_i)\}_{i=1}^N$). The goal of a regression model is to find the best-fit function $f(x_i)$ that predicts the response values. The Gaussian Process Regression (GPR) and regularized least-squares regression using a least absolute shrinkage and selection operator (LSR-Lasso) models are the two example regression methods used in the present disclosure.

Gaussian Process Regression (GPR)

GPR is a non-parametric regression method, as described in C. E. Rasmussen and C. K. I. Williams, *Gaussian Processes for Machine Learning*. MIT Press, Boston, 2006, which is hereby incorporated by reference herein. The objective of GPR is to model the dependency as follows:

$$y_i = f(x_i) + \varepsilon_i \quad (4)$$

where $\varepsilon_i = N(0, \sigma_n^2)$ is the independent and identically and normally distributed noise terms. GPR has two main advantages compared to conventional regression methods, including: 1) It is a non-parametric regression method and the model structure is determined from data; and, 2) It uses a probabilistic approach that can model the prediction uncertainty.

A Gaussian process is completely identified by its mean $\mu(x_i)$ and covariance function $\Sigma(x_i, x_j)$. The covariance function used in here is a parameterized squared exponential (SE) covariance function:

$$\Sigma(x_i, x_j) = \sigma_f^2 \exp(-\tfrac{1}{2}(x_i - x_j) W^{-1} (x_i - x_j)^T) \quad (5)$$

where $\sigma_f$ is the signal variance and $W = \text{diag}(l_1, \ldots, l_D)$ is the diagonal matrix of length-scale parameters. This covariance function implements automatic relevance determination (ARD) since the length-scale values determine the effect of each predictor on the regression.

Assuming N training samples are available, for a new input, $x^*$, the covariance matrix in equation (5) above can be partitioned into two blocks:

$$\sum_{N+1} = \begin{pmatrix} \sum_N & \sum_{N^*} \\ \sum_{N^*}^T & \alpha \end{pmatrix} \quad (6)$$

where $\Sigma_N$ is the N×N covariance matrix of the training samples; $\Sigma_{N^*}$ includes the elements of $\Sigma(x_i, x^*)$ and $\alpha$ represents $\Sigma(x^*, x^*)$. A posteriori mean estimation and related variance can be given respectively by:

$$\mu(x^*) = \Sigma_{N^*} \Sigma_N^{-1} y \quad (7)$$

$$\sigma^2(x^*) = \alpha - \Sigma_{N^*}^T \Sigma_N^{-1} \Sigma_{N^*} \quad (8)$$

where $y = [y_1, \ldots, y_N]^T$.

Regularized Least-Squares Regression Using Lasso (LSR-Lasso)

The Lasso (least absolute shrinkage and selection operator) is a shrinkage and selection method for regularized linear regression. LSR-Lasso is a parametric regression technique, described in R. Tibshirani, "Regression Selection and Shrinkage via the Lasso," *J. R. Statist. Soc. B*, vol. 58., no. 1, pp. 267-288, 1996, which is hereby incorporated by reference herein. LSR-Lasso minimizes the usual sum of squared errors, with a bound on the sum of the absolute values of the coefficients to deliver a sparse solution, i.e. a set of estimated regression coefficients in which only a small number are non-zero. Given a linear regression, the LSR-Lasso solves the $\ell_1$-penalized regression so as to minimize:

$$\frac{1}{2} \sum_{i=1}^N (y_i - \beta_0 - x_i^T \beta)^2 + \lambda \sum_{j=1}^D |\beta_j| \quad (9)$$

for unknown parameters $\beta_0$ and $\beta = [\beta_1, \ldots, \beta_D]$. The second term in equation (9) is the penalty function balancing the fit of the model with its complexity with the non-negative parameter $\lambda$ governing this trade-off. The value $\lambda$ of is chosen based on 10-fold cross-validation in the present disclosure. LSR-Lasso is used in the comparisons discussed below to provide a performance baseline for GPR with the SE-ARD covariance function.

Example Method

Figure 3:
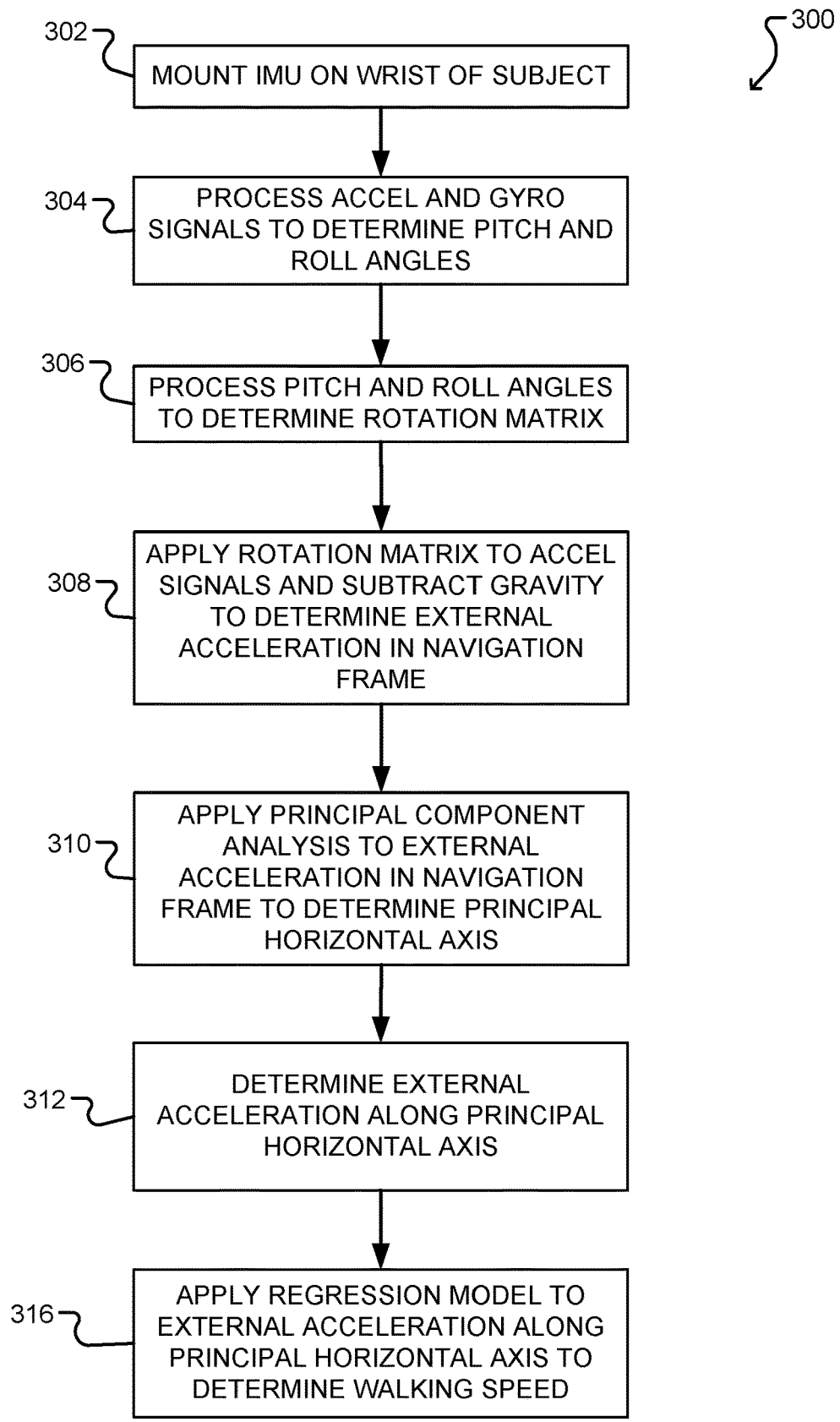
FIG. 3 is a flowchart illustrating steps of an example walking speed estimation method according to one embodiment.

FIG. 3 shows an example method 300 for estimating walking seed according to one embodiment. The method 300 begins with mounting an IMU on the subject's wrist, and calibrating/initializing the system at step 302.

At step 304, acceleration and rate of turn signals from the IMU are processed to determine pitch and roll angles. At step 306 the pitch and roll angles are processed to determine the rotation matrix $_s^nR_{tilt}$ from the s-frame to the n-frame. At step 308 the rotation matrix is applied to the acceleration signals from the IMU, and gravitational acceleration is subtracted, to determine the external acceleration in the n-frame $^na_{ext}$.

At step 310, the external acceleration in the n-frame $^na_{ext}$ is subjected to principal component analysis to determine the principal horizontal axis. At step 312 the the external acceleration along the principal horizontal axis (pca-acc) is determined. At step 316 a regression model is applied using external acceleration along the principal horizontal axis (pca-acc) to determine an estimated walking speed.

Experimental Results and Discussion

As discussed above, signals representing three different variables can be used to estimate walking speed, namely the magnitude of 3D acceleration (acc), the magnitude of external acceleration (ext-acc) and the external acceleration in the principal axis (pca-acc, which is used in systems and methods according to the present disclosure). A signal representing each of the above mentioned three variable streams is divided into 5-s epochs. Within each epoch, the following time-domain and frequency-domain features are calculated.

Time-domain (TD) features: The time-domain features used in this study include the statistical features consisting of standard deviation, median, mod, mean of absolute values, plus other features including number of mean crossing, signal magnitude area ($\Sigma_{n=1}^{N}|x[n]|$), and energy ($\Sigma_{n=1}^{N}x^2[n]$).

Frequency-domain (FD) features: A 512-point fast Fourier transform (FFT) is used within each epoch to obtain frequency information. The first forty coefficients of the single-sided amplitude spectrum are used as FD features. These forty coefficients correspond to the frequency range of less than 8 Hz. This frequency range is selected based on inspection of the Fourier transforms from the 15 subjects.

Two modeling approaches are compared in the present disclosure: a generalized model versus a subject-specific model. Considering N subjects, to train and test the models, for each subject 20% of the subject-specific dataset (of the short indoor tests) is randomly sampled and partitioned into test data, the remaining fraction constituting training data. For each model, the process was repeated for 10 times for different randomly sampled data and results were averaged. The final reported error is the error averaged across all participants.

Generalized model: The generalized model for subject n was trained using all data from the remaining subjects and predictions were made on subject n's test data. For the generalized models, along with TD and FD feature sets, two anthropomorphic parameters including height and weight of the subjects are included in the input features.

Subject-specific model: The subject-specific model for subject n was trained using subject n's training data and was tested on subject n's test data.

Figure 4:
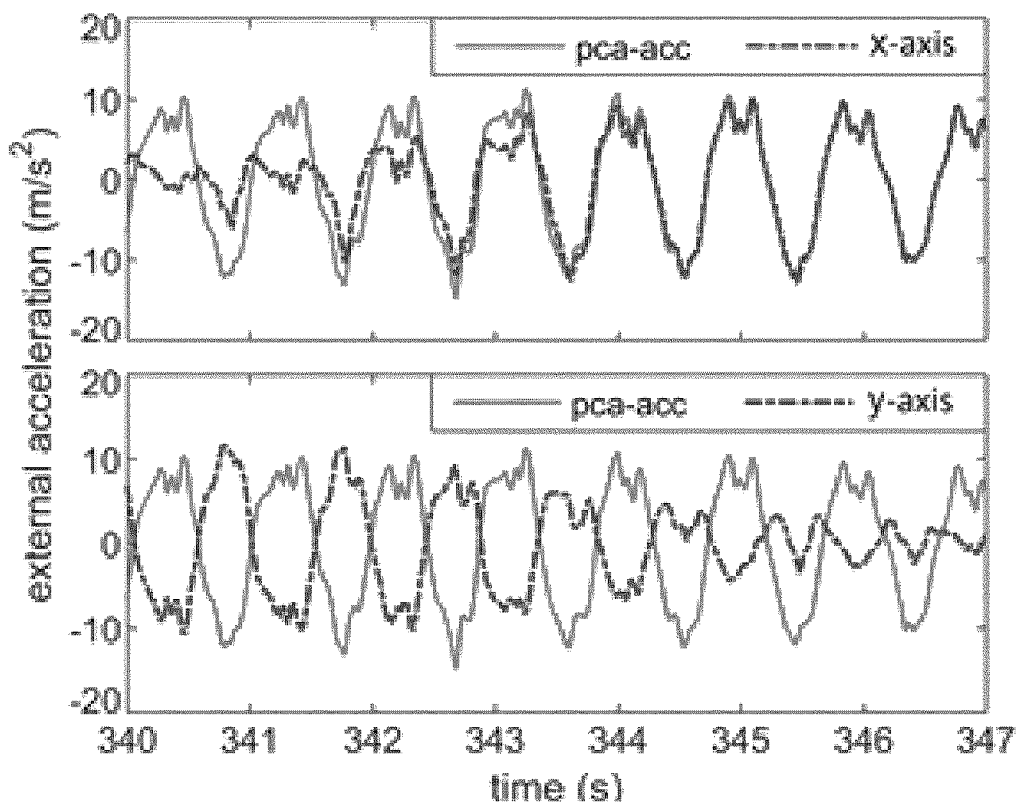
FIG. 4 is a series of graphs comparing the horizontal components of external acceleration in the x- and y-axes of the n-frame to the external acceleration along the principal horizontal axis.

A. Effect of the PCA on external acceleration signal: FIG. 4 shows the horizontal components of the external acceleration in the directions of x-axis of the n-frame (top graph) and y-axis of the n-frame (bottom graph) in addition to the acceleration along the direction of the principal axis (pca-acc) during 7 s of the 10-minute outdoor walking trial. In FIG. 4, amplitude of the acceleration in the x-axis grows whereas the one in the y-axis shrinks (happening when the walking direction changes). However, since the pca-acc signal always captures the acceleration in the principal axis (pointing toward the direction of motion), the amplitude of the pca-acc signal remains constant when the walking speed is constant but the direction changes, as shown in FIG. 4. Thus, the pca-acc signal is expected to provide better estimates of walking speed compared to the external acceleration signal in each axis.

Figure 5:
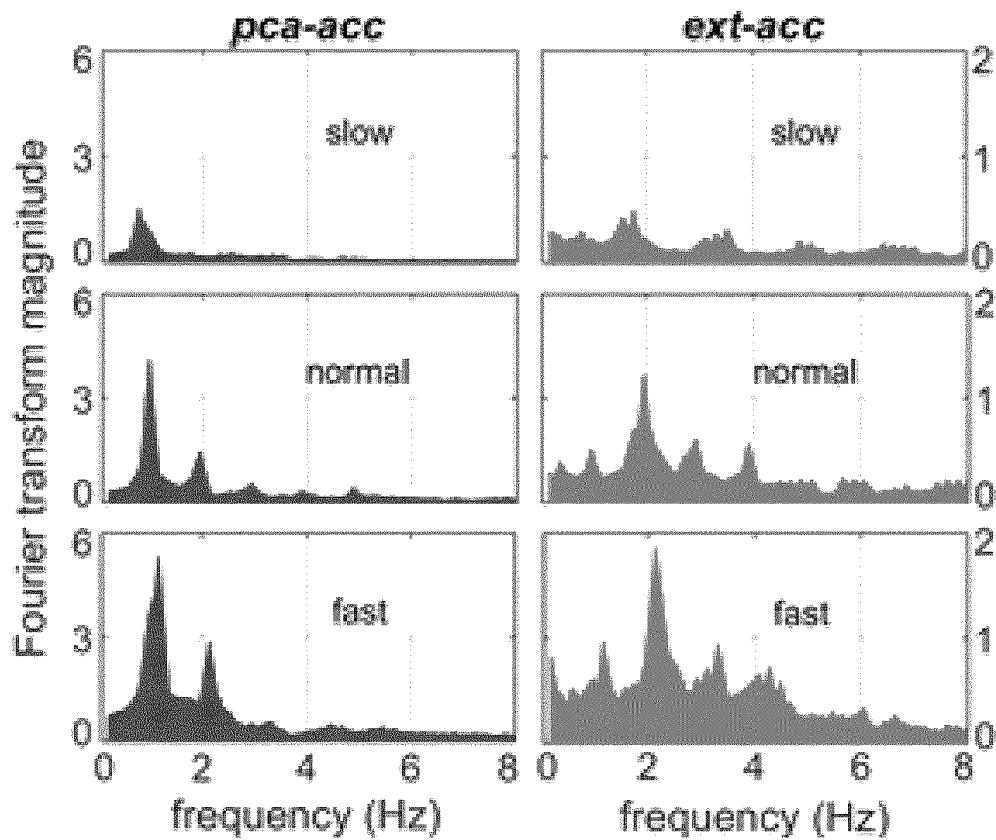
FIG. 5 is a series of graphs comparing frequency domain components of the magnitude of external acceleration and the external acceleration along the principal horizontal axis at different walking speeds.

On the other hand, the magnitude of 3D external acceleration (ext-acc) is another signal that will get affected less significantly by the changes in walking direction compared to the acceleration in individual axes. In FIG. 5, the pca-acc and ext-acc signals are compared to each other in the frequency-domain. FIG. 5 shows the Fourier transform magnitude for both the pca-acc and ext-acc signals for the three different walking speed regimes (slow, normal and fast) based on the dataset collected from one subject. Based on FIG. 5, compared to ext-acc, the pca-acc signal shares a relatively more distinct pattern of peaks between the three walking regimes with the corresponding peaks moving to the higher frequencies and growing in amplitude as the walking speed gets faster. Thus, it is expected that the pca-acc signal will provide more accurate estimation of the walking speed compared to the ext-acc signal.

B. Performance of the generalized GPR model: Table I shows the walking speed estimation accuracy of the generalized GPR model for signals representing the three different variables: pca-acc, ext-acc and acc. In this table, the reported mean absolute error (MAE) and the root mean square error (RMSE) are used as measures of accuracy and the standard deviation (SD) shows the precision. Based on this table, when using the pca-acc variable, MAE and RMSE are about 5.9 (±4.7)% and 7.9 (±5.6) cm/s, respectively. Compared to the ext-acc and acc variables, employing pca-acc results in significantly better estimation accuracy. Using analysis of variants (ANOVA), p<0.01 shows that the results are statistically significant.

TABLE I

Evaluation of the walking speed estimation error based on generalized GPR model for various variables and features sets.

| | Combined FD and TD Features | | | | TD Features Only | | | |
|---|---|---|---|---|---|---|---|---|
| Variable | MAE (%) | SD (%) | RMSE (cm/s) | SD (cm/s) | MAE (%) | SD (%) | RMSE (cm/s) | SD (cm/s) |
| pca-acc | 5.9 | 4.7 | 7.9 | 5.6 | 15.6 | 7.0 | 17.3 | 7.5 |
| ext-acc | 12.13 | 6.97 | 14.57 | 7.78 | 11.8 | 6.98 | 14.5 | 8.28 |
| acc | 14.4 | 8.26 | 16.53 | 8.49 | 14.24 | 6.89 | 14.3 | 7.66 |

Also shown in Table I is the walking speed estimation errors when FD features are not being used (the two anthropomorphic features are used in both cases) in the generalized GPR model. As it can be seen, the effect of removing the FD features on the accuracy obtained by the ext-acc and acc variables is negligible (changes in MAE is <1%), whereas for pca-acc, the accuracy is changed from 5.9% to 15.6%. This shows that the variations in the frequency spectrum of the pca-acc signal (which in turn is correlated to the changes in frequency and amplitude of arm swing) is highly correlated to walking speed.

Figure 6:
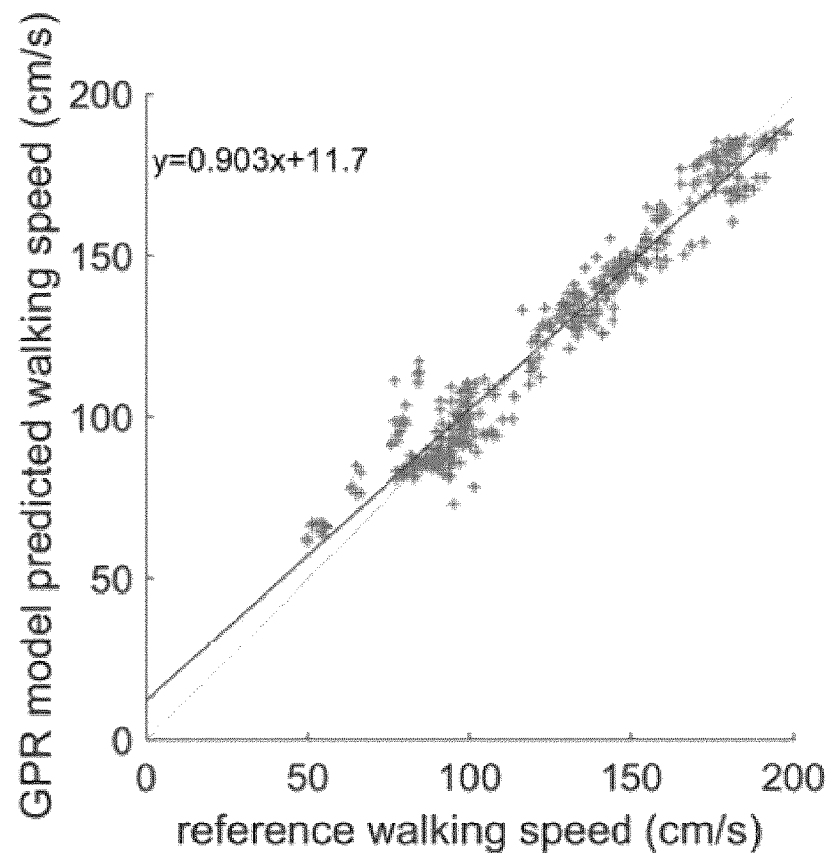
FIG. 6 shows a regression analysis using a Gaussian process regression (GPR) for estimating walking speed using the external acceleration along the principal horizontal axis.
Figure 7:
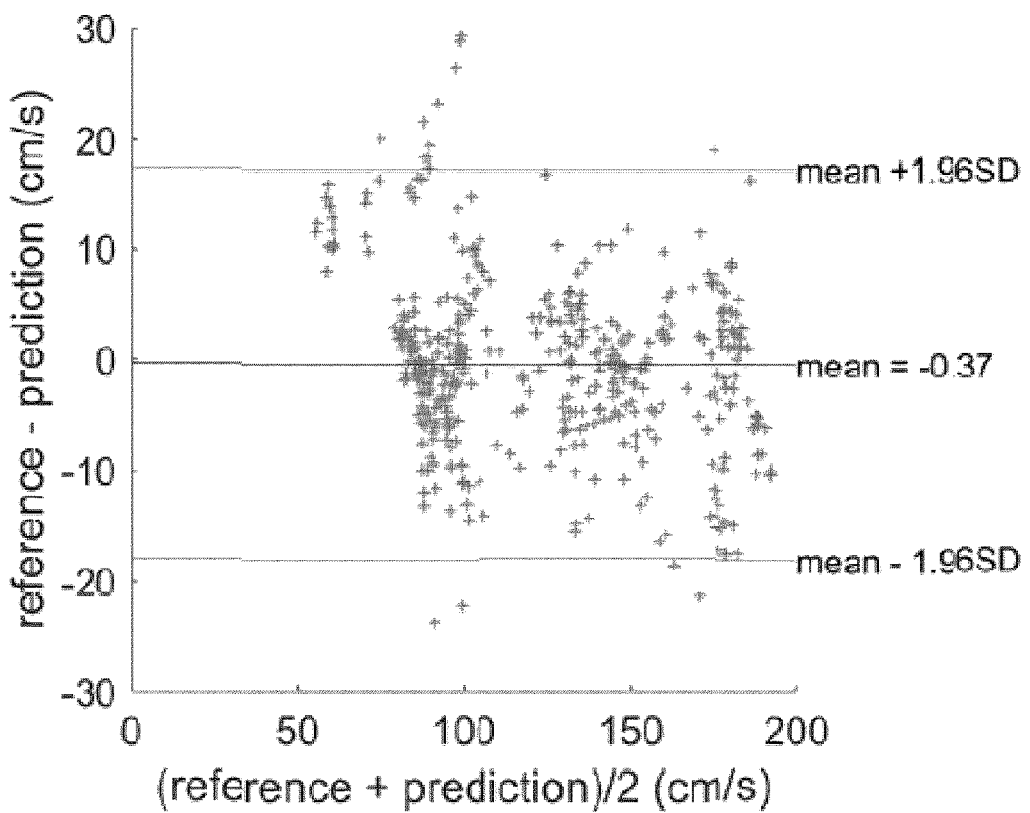
FIG. 7 shows a Bland-Altman plot using a GPR for estimating walking speed using the external acceleration along the principal horizontal axis.

The regression analysis and Bland-Altman plots for the predicted walking speed values based on GPR generalized model, using the pca-acc signal (and combined FD and TD features) are shown in FIGS. 6 and 7 respectively. The regression shows a very strong linear correlation between the predicted and reference walking speed values (Pearson's r=0.9742, p<0.001). The Bland-Altman plot shows that, except for a few outliers (mainly at the lower speed range), the error is mainly kept within 95% limits of agreement and that there is no significant systematic dependence of the estimation error on the walking speed. The obtained accuracy by using the pca-acc signal is better than the MAE of 6.96% in Hagler S, Austin D, Hayes T L, Kaye J, Pavel M. "Unobtrusive and ubiquitous in-home monitoring: a methodology for continuous assessment of gait velocity in elders." *IEEE Trans. Biomed. Eng.* 2010; 57(4): 813-20, which uses ceiling-mounted RF transceivers, and the RMSE of 8 to 15 cm/s in Jacobs P G, Wan E A, Schafermeyer E, Adenwala F. "Measuring In-Home Walking Speed using Wall-Mounted RF Transceiver Arrays." *Proc. IEEE Eng. Med. Biol. Soc.* 2014 August; Chicago, Ill. p. 914-17, which used wall-mounted RF transceivers for longitudinal in-home walking speed monitoring used for early detection of MCI. The positive results described herein demonstrate the potential of the proposed wrist-worn methods and systems for monitoring of walking speed as an early marker of health issues. Compared to the systems based on the ceiling and wall-mounted sensors in the studies referred to above, which are only applicable to confined hallways in single resident homes, the proposed methods and systems offer the advantage of being self-contained and can be easily used indoor/outdoor environments. Since the best walking speed estimation accuracy is obtained by using the pca-acc signal and a combination of FD and TD features, the reported results in the following sections are based on the same variables and feature sets.

C. Comparison between the generalized GPR and subject-specific GPR models: Table II shows the walking speed estimation errors for the generalized and subject-specific GPR models in various walking speed regimes: slow (50-100 cm/s), normal (100-150 cm/s) and fast (150-200 cm/s). Based on this table, the generalized and subject-specific models have very similar performances for normal and fast walking speed regimes. However, for the slow walking regime, the RMSE of the generalized model is about 7.5 cm/s (MAE of 8.9%) whereas the RMSE for the subject-specific model is about 2.6 cm/s (MAE of 2.6%). This can be explained as follows: the generalized model has to fit the model simultaneously across subjects and within each subject. Compared to normal and fast walking, in slow walking both the frequency and amplitude of arm swing is very weak and for most subjects the arm swing differs the most at their lowest walking speeds. Intuitively, given that the generalized model has to trade-off between overall accuracy and subject-specific accuracy, the model is optimized over the most similar input points which correspond to arm swing motion in normal and fast walking regimes. To shed further light on this issue, a separate generalized model is trained for the slow walking regime by excluding the data points correspond to the velocities of above 100 cm/s. Results show that this new model can reduce the RMSE to 5.1 cm/s (and the MAE to 6.2%). This observation suggests that if one is interested in estimating slow walking speeds (e.g., tracking walking speed of the elderly) a model that is trained specifically for the speed regime of interest may provide a better accuracy.

TABLE II

Comparison between generalized GPR and subject-specific GPR models in walking speed estimation for various speed regimes: slow (50-100 cm/s), normal (100-150 cm/s) and fast (150-200 cm/s).

| | Generalized Model | | | | Subject-Specific Model | | | |
|---|---|---|---|---|---|---|---|---|
| Speed regime | MAE (%) | SD (%) | RMSE (cm/s) | SD (cm/s) | MAE (%) | SD (%) | RMSE (cm/s) | SD (cm/s) |
| Slow | 8.9 | 5.6 | 7.5 | 4.2 | 2.6 | 3.3 | 2.6 | 2.6 |
| Normal | 4.4 | 4.3 | 6.6 | 5.3 | 4.5 | 5.5 | 7.3 | 7.0 |
| Fast | 4.5 | 4.1 | 9.5 | 7.3 | 4.5 | 3.2 | 8.1 | 5.5 |

Figure 8:
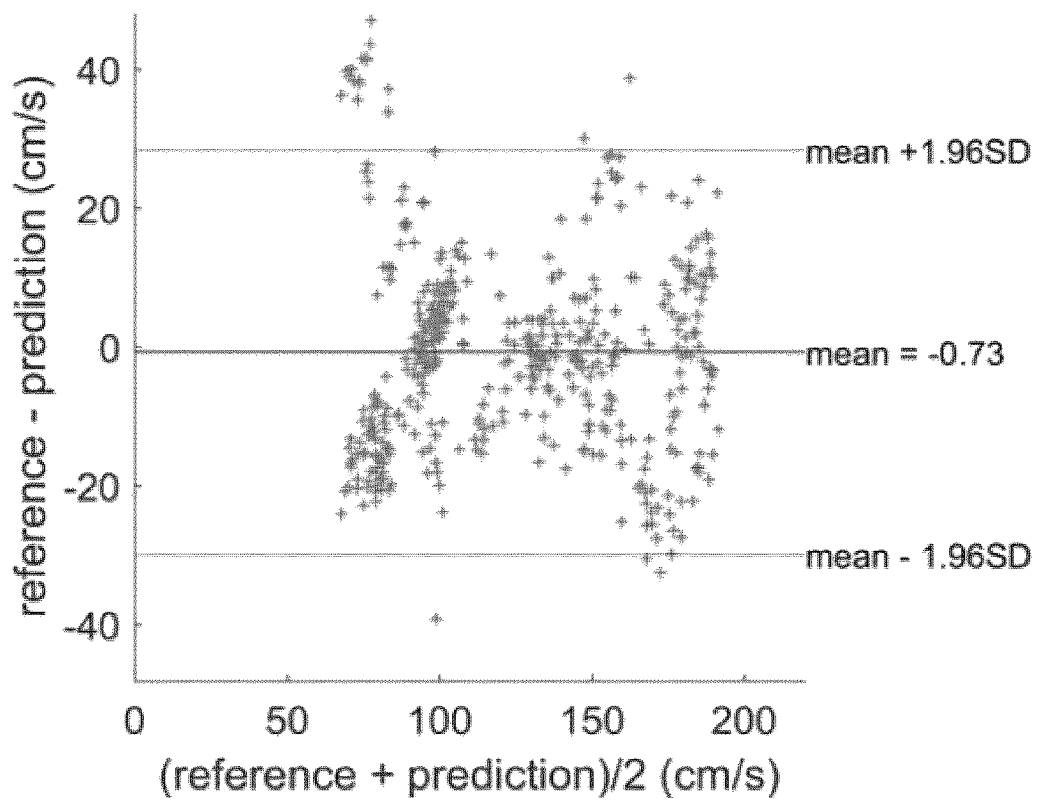
FIG. 8 shows a Bland-Altman plot using a least square regression based on Lasso (LSR-Lasso) for estimating walking speed using the external acceleration along the principal horizontal axis.

D. Performance of the generalized LSR-Lasso model: FIG. 8 shows the Bland-Altman plots for the predicted walking speed values based on generalized LSR-Lasso model. Similar to the generalized GPR model, outliers are mainly in the lower speed range and the error is mainly kept within 95% limits of agreement. RMSE of the estimated walking speed is about 10.7 cm/s (SD=7 cm/s) and the MAE is 12.78% (SD=7.7%). Compared to the generalized GPR model, the LSR-Lasso model has a larger prediction error (p<0.01). This comparison shows that the data-driven estimation of the model structure in the GPR model can more effectively capture the influence of each input feature on the output walking speed.

Better performance of the GPR model compared to the LSR model has also been observed in Dadashi F, Millet G P, Aminian K. "A Bayesian approach for pervasive estimation of breaststroke velocity using a wearable IMU." *Pervasive Mob. Comput.* 2015; 19: 37-46 where the generalized GPR and LSR models are used to estimate swimming velocity using a waist-worn IMU. In general, once the model is learnt, the computational complexity of a nonparametric approach such as GPR for a new estimation depends on the number of training data points (N) and is of order $O(N^3)$; whereas the one for the parametric approaches such as LSR-Lasso depends on the dimension of the input data space (d) and is of order $O(d^3)$. The computational cost can be an important factor when implementing these algorithms in resource-constrained platforms such as wearable devices.

Figure 9:
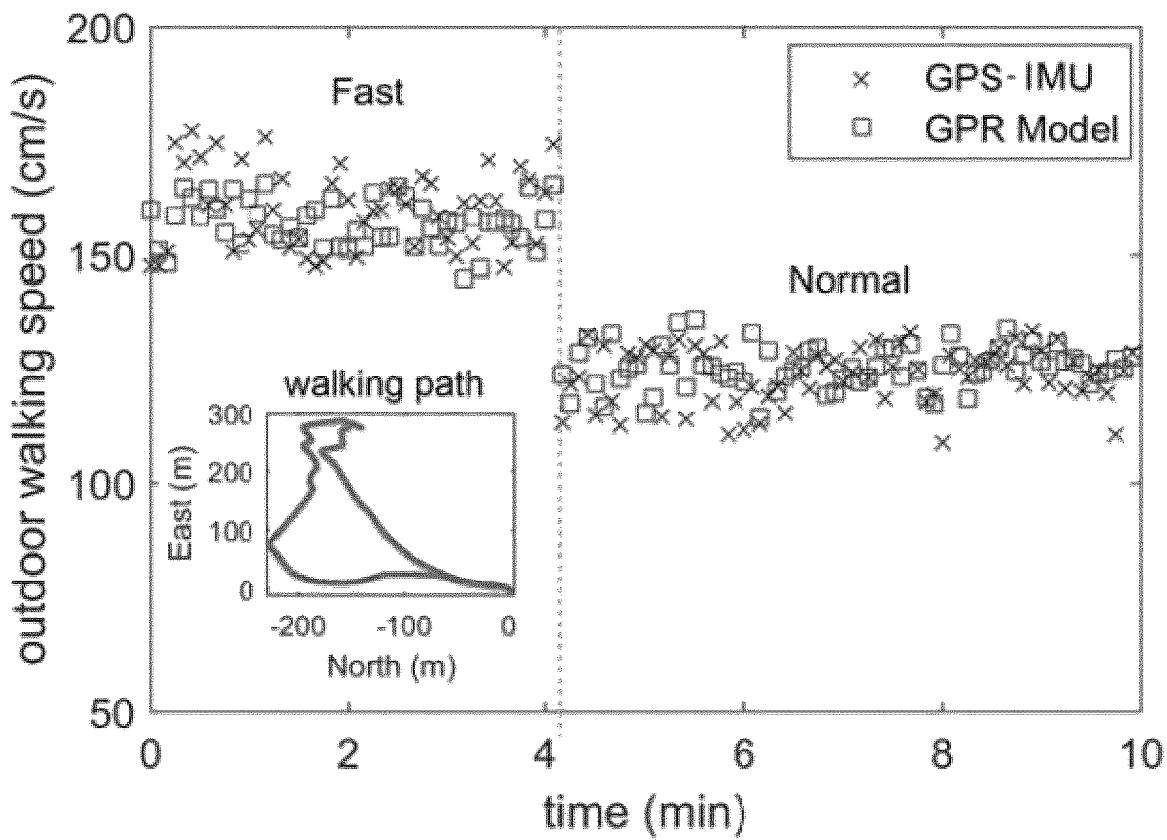
FIG. 9 shows walking speed estimation results based on a generalized GPR model using the external acceleration along the principal horizontal axis in comparison to a reference speed obtained by GPS-IMU fusion.

E. Testing of the generalized GPR model on outdoor free walking data: In this section, the experimental data from the 10-minute outdoor free walking trial of subject 1 is used to examine how well the trained generalized GPR model (based on short indoor walking trials that are limited to straight-line walking) will perform for wrist-based walking speed estimation in a real-world environment (where the walking path is not limited to a straight line). FIG. 9 shows the estimated outdoor walking speed along with a reference speed a GPS-IMU fusion algorithm as described above, which is more accurate than using GPS alone, for normal and fast walking speed regimes during the 10-minute trial. FIG. 9 shows that the predicted walking speed based on the generalized GPR model is highly correlated to the GPS walking speed (Pearson's r=0.901, p<0.001). It can be seen that the generalized GPR model can clearly differentiate between the fast and slow walking regimes. The variations of walking speed within each speed regime is as expected considering the various turns in the walking path (shown in the inset of FIG. 9) and the natural variations in free walking speed over time.

Conclusion

Regression model-based human walking speed estimation methods and system are presented which use the inertial data from a wrist-worn IMU. The arm swing motion is determined based on a principal component acceleration signal representing a novel variable called pca-acc, which is highly correlated to walking speed in terms of both temporal and frequency characteristics. To obtain the principal component acceleration signal, first the tilt angles of the wrist are calculated by applying a Kalman filter-based sensor fusion method. Second, principal component analysis (PCA) is employed to find the horizontal acceleration in the direction of arm swing. Experimental results from 15 young subjects showed that using the proposed principal component acceleration signal will result in significantly better walking speed estimation accuracy compared to the use of raw acceleration variables ($p<0.01$). Using combined time domain (TD) and frequency domain (FD) features of the principal component acceleration signal, a generalized Gaussian process regression (GPR) model resulted in accuracy and precision of about 5.9% and 4.7% respectively. Based on the experimental results, the generalized and subject-specific GPR models tend to perform similar except for slow walking regime (speed <100 cm/s) where a subject-specific model provided better estimation accuracy. Compared to the generalized least square regression model based on Lasso (LSR-Lasso), the generalized GPR model performed significantly better ($p<0.01$) for wrist-based walking speed estimation. Experimental results from a 10-minute outdoor walking trial demonstrated the feasibility of using the proposed methods and systems for wrist-based walking speed estimation in real-world environments.

REFERENCES

The following references, each of which are incorporated by reference herein, are related to the subject matter of the present disclosure:

1. Akl A, Taati B, Mihailidis A. Autonomous unobtrusive detection of mild cognitive impairment in older adults. IEEE Trans. Biomed. Eng. 2015; 62(5):1383-94.
2. Dodge H H, Mattek N C, Austin D, Hayes T I, Kaye J A. In-home walking speeds and variability trajectories associated with mild cognitive impairment. Neurology. 2012; 78(24):1946-52.
3. Akl A, Mihailidis A. Estimating in-home walking speed distributions for unobtrusive detection of mild cognitive impairment in older adults. Proc. IEEE Eng. Med. Biol. Soc. 2015 August; Milan, Italy. p. 5175-78.
4. Heesen C, Bohm J, Reich C, Kasper J, Goebel M, Gold S M. Patient perception of bodily functions in multiple sclerosis: gait and visual function are the most valuable. Mult Soler. 2008; 14(7):988-91.
5. Graham J E, Ostir G V, Fisher S R, Ottenbacher K J. Assessing walking speed in clinical research: a systematic review. J. Eval. Clin. Pract. 2016; 14(4):552-62.
6. Bayle N, Patel AS, Crisan D, Guo L J, Hutin E, Weisz D J, et al. Contribution of Step Length to Increase Walking and Turning Speed as a Marker of Parkinson's Disease Progression. PLoS One. 2016; 11(4):e0152469.
7. Bautmans I, Jansen B, Keymolen B V, Mets T. Reliability and clinical correlates of 3D-accelerometry based gait analysis outcomes according to age and fall-risk. Gait Posture. 2011; 33(3): 366-72.
8. Abe Y, Matsunaga A, Matsuzawa R, Kutsuna T, Yamamoto S, Yoneki K, et al. Determinants of Slow Walking Speed in Ambulatory Patients Undergoing Maintenance Hemodialysis. PLoS One. 2016; 11(3): e0151037.
9. Robertson D A, Savva G M A, King-Kallimanis B L, Kenny R A. Negative perceptions of aging and decline in walking speed: A self-fulfilling prophecy. PLoS One. 2015; 10(4): e0123260.
10. Fritz S, Lusardi M. Walking speed: the sixth vital sign. J. Geriatr. Phys. Ther. 2009; 32(2): 46-9.
11. Studenski S, Perera S, Patel K, Rosano C, Faulkner K, Inzitari, M, et al. Gait speed and survival in older adults. J. American Medical Association (JAMA). 2011; 305(1): 50-8.
12. Maggio M, Ceda G P, Ticinesi A, De Vita F, Gelmini G, Costantino C, et al. Instrumental and Non-Instrumental Evaluation of 4-Meter Walking Speed in Older Individuals. PLoS One. 2016; 11(4): e0153583.
13. Schimpl M, Lederer C, Daumer M. Development and validation of a new method to measure walking speed in free-living environments using the actibelt® platform. PLoS One. 2011; 6(8): e23080.
14. Greene B R, Kenny R A. Assessment of cognitive decline through quantitative analysis of the timed up and go test. IEEE Trans. Biomed. Eng. 2012; 59(4): 988-95.
15. Vaney C, Blaurock H, Gattlen B, Meisels C. Assessing mobility in multiple sclerosis using the Rivermead Mobility Index and gait speed. Clin. Rehabil. 1996; 10(3): 216-26.
16. Enright P L, McBurnie M A, Bittner V, Tracy R P, McNamara R, Arnold A, et al. The 6-min Walk Test A Quick Measure of Functional Status in Elderly Adults. Chest J. 2003; 123(2): 387-98.
17. Schimpl M, Moore C, Lederer C, Neuhaus A, Sambrook J, Danesh J, et al. Association between Walking Speed and Age in Healthy, Free-Living Individuals Using Mobile Accelerometry—A Cross-Sectional Study. PLoS One. 2011; 6(8): e23299.
18. Hagler S, Austin D, Hayes T L, Kaye J, Pavel M. Unobtrusive and ubiquitous in-home monitoring: a methodology for continuous assessment of gait velocity in elders. IEEE Trans. Biomed. Eng. 2010; 57(4): 813-20.
19. Jacobs P G, Wan E A, Schafermeyer E, Adenwala F. Measuring In-Home Walking Speed using Wall-Mounted RF Transceiver Arrays. Proc. IEEE Eng. Med. Biol. Soc. 2014 August; Chicago, Ill. p. 914-17.
20. Wang F, Stone E, Skubic M, Keller J M, Abbott C, Rantz M. Toward a passive low-cost in-home gait assessment system for older adults. Proc. IEEE J. Biomed. Heal. Informatics. 2013; 17(2): 346-55.
21. Zihajehzadeh S, Park E J. A novel biomechanical model-aided IMU/UWB fusion for magnetometer-free lower body motion capture. IEEE Trans. Syst., Man, Cybern: Syst. 2016; DOI: 10.1109/TSMC.2016.2521823.
22. Loh D, Lee T J, Zihajehzadeh S, Hoskinson R, Park E J. Fitness activity classification by using multiclass support vector machines on head-worn sensors. Proc. IEEE Eng. Med. Biol. Soc. 2015 August; Milan, Italy. p. 502-5.
23. Lee J K, Park E J. A fast quaternion-based orientation optimizer via virtual rotation for human motion tracking. IEEE Trans. Biomed. Eng. 2009; 56(5): 1574-82.

24. Elhoushi M, Georgy J, Noureldin A, Korenberg M J. Motion mode recognition for indoor pedestrian navigation using portable devices. IEEE Trans. Instrum. Meas. 2016; 65(1): 208-221.

25. Ligorio G, Sabatini A M. A novel kalman filter for human motion tracking with an inertial-based dynamic inclinometer. IEEE Trans. Biomed. Eng. 2015; 62(8): 2033-43.

26. Laudanski A, Yang S, Li Q. A concurrent comparison of inertia sensor-based walking speed estimation methods. Proc. IEEE Eng. Med. Biol. Soc. 2011 August; Boston, Mass. p. 3484-87.

27. Zihajehzadeh S, Loh D, Lee T J, Hoskinson R, Park E J. A cascaded Kalman filter-based GPS/MEMS-IMU integration for sports applications. Measurement. 2015; 73: 200-210.

28. Foxlin E. Pedestrian tracking with shoe-mounted inertial sensors. IEEE Comput. Graph. Appl. 2005; 25(6): 38-46.

29. Meng X, Zhang Z Q, Wu J K, Wong W C. Hierarchical information fusion for global displacement estimation in microsensor motion capture. IEEE Trans. Biomed. Eng. 2013; 60(7): 2052-63.

30. Skog I, Peter H, Nilsson J, Rantakokko J. Zero-velocity detection—An algorithm evaluation. IEEE Trans. Biomed. Eng. 2010; 57(11): 2657-66 .

31. Hu J S, Sun K C, Cheng C Y. A Kinematic Human-Walking Model for the Normal-Gait-Speed Estimation Using Tri-Axial Acceleration Signals at Waist Location. IEEE Trans. Biomed. Eng. 2013; 60(8): 2271-79.

32. Vathsangam H, Emken B A, Spruijt-Metz D, Sukhatme G S. Toward free-living walking speed estimation using Gaussian Process-based Regression with on-body accelerometers and gyroscopes. Proc. Pervasive Comput. Technol. Healthc. 2010 March; Munich, Germany. p. 1-8.

33. Dadashi F, Millet G P, Aminian K. A Bayesian approach for pervasive estimation of breaststroke velocity using a wearable IMU. Pervasive Mob. Comput. 2015; 19: 37-46.

34. Rasmussen C C, Williams C K, Gaussian Processes for Machine Learning. MIT Press; Boston, 2006.

35. Vathsangam H, Emken A, Schroeder E T, Spruijt-Metz D, Sukhatme G S. Determining energy expenditure from treadmill walking using hip-worn inertial sensors: an experimental study. IEEE Trans. Biomed. Eng. 2011; 58(10): 2804-15.

36. Tibshirani R. Regression Selection and Shrinkage via the Lasso. J. R. Statist. Soc. B. 1996; 58(1): 267-288.

37. Zihajehzadeh S, Loh D, Lee T J, Hoskinson R, Park E J. A cascaded two-step Kalman filter for estimation of human body segment orientation using MEMS-IMU. Proc. IEEE Eng. Med. Biol. Soc. 2014 August; Chicago, Ill. p. 6270-73.

38. Zihajehzadeh S, Lee T J, Lee J K, Hoskinson R, Park E J. Integration of MEMS Inertial and Pressure Sensors for Vertical Trajectory Determination. IEEE Trans. Instrum. Meas. 2015; 64(3): 804-14.

39. Lee J K, Park E J, Robinovitch S N. Estimation of attitude and external acceleration using inertial sensor measurement during various dynamic conditions. IEEE Trans. Instrum. Meas. 2012; 61(8): 2262-73.

40. Jolliffe I T, Principal Component Analysis. New York: Springer Verlag, 2002.

41. Vathsangam H, Emken B A, Schroeder E T, Spruijt-Metz D, Sukhatme G S. Towards a generalized regression model for on-body energy prediction from treadmill walking. Proc. Pervasive Comput. Technol. Healthc. 2011 June; Dublin, Ireland. p. 168-75.

The present disclosure may be embodied in other specific forms without departing from its spirit or essential characteristics. The described embodiments are to be considered in all respects only as illustrative and not restrictive.

As will be apparent to those skilled in the art in light of the foregoing disclosure, many alterations and modifications are possible to the methods and systems described herein. While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are may reasonably be inferred by one skilled in the art. The scope of the claims should not be limited by the embodiments set forth in the examples, but should be given the broadest interpretation consistent with the foregoing disclosure.

The invention claimed is:

1. A system for estimating walking speed of a subject, the system comprising:
   an inertial measurement unit (IMU) mounted on a wrist of the subject, the IMU comprising an accelerometer and a gyroscope and configured to output rate of turn signals and acceleration signals; and,
   a processing system in communication with the IMU to receive the rate of turn and acceleration signals, the processing system comprising:
      a sensor fusion block configured to process the rate of turn and acceleration signals from the IMU to generate a pitch angle and a roll angle;
      a rotation matrix calculation block configured to process the pitch angle and the roll angle to generate a rotation matrix from a sensor frame of the IMU to a navigation frame of the subject;
      an acceleration vector transformation block configured to apply the rotation matrix to the acceleration signals and remove gravitational acceleration to generate an external acceleration signal;
      a principal component analysis block configured to process the external acceleration signal to determine a principal horizontal axis;
      a principal component extraction block configured to process the external acceleration signal to generate a principal component acceleration signal representing external acceleration along the principal horizontal axis; and
      a walking speed estimation block configured to process the principal component acceleration signal using a regression-based method to determine an estimated walking speed of the subject.

2. The system of claim 1 wherein the walking speed estimation block uses a Gaussian process regression model.

3. The system of claim 1 wherein the walking speed estimation block uses a regularized least square regression using a least absolute shrinkage and selection operator model.

4. The system of claim 1 wherein the walking speed estimation block uses a generalized regression model trained with data from a plurality of different subjects.

5. The system of claim 1 wherein the walking speed estimation block uses a subject-specific regression model trained with data from the subject.

6. A method for estimating a walking speed of a subject, the method comprising:
mounting an inertial measurement unit (IMU) on a wrist of the subject, the IMU configured to generate acceleration and rate of turn signals;
processing the acceleration and rate of turn signals from the IMU to generate a pitch angle and a roll angle;
processing the pitch angle and the roll angle to generate a rotation matrix from a sensor frame of the IMU to a navigation frame of the subject;
applying the rotation matrix to the acceleration signals and removing gravitational acceleration to generate an external acceleration signal;
processing the external acceleration signal to determine a principal horizontal axis and to generate a principal component acceleration signal representing external acceleration along the principal horizontal axis; and
processing the principal component acceleration signal using a regression-based method to determine an estimated walking speed of the subject.

7. The method of claim 6 wherein using the regression-based method comprises applying a Gaussian process regression model.

8. The method of claim 6 wherein using the regression-based method comprises applying a regularized least square regression using a least absolute shrinkage and selection operator model.

9. The method of claim 6 wherein using the regression-based method comprises applying a generalized regression model trained with data from a plurality of different subjects.

10. The method of claim 6 wherein using the regression-based method comprises applying a subject-specific regression model trained with data from the subject.

* * * * *